United States Patent [19]

Hess

[11] 4,285,347
[45] Aug. 25, 1981

[54] STABILIZED DIRECTIONAL NEURAL ELECTRODE LEAD

[75] Inventor: Stanley R. Hess, Miami, Fla.

[73] Assignee: Cordis Corporation, Miami, Fla.

[21] Appl. No.: 60,577

[22] Filed: Jul. 25, 1979

[51] Int. Cl.³ .............................................. A61N 1/04
[52] U.S. Cl. ................................... 128/785; 128/786
[58] Field of Search ............ 128/784, 785, 786, 419 P, 128/419 C, 419 R

[56] References Cited

U.S. PATENT DOCUMENTS

| | | | |
|---|---|---|---|
| 3,729,008 | 4/1973 | Berkovits | 128/785 |
| 4,044,774 | 8/1977 | Corbin et al. | 128/784 |
| 4,057,067 | 11/1977 | Lajos | 128/785 |
| 4,136,703 | 1/1979 | Wittkampf | 128/419 P |
| 4,141,365 | 2/1979 | Fishell et al. | 128/419 R X |
| 4,154,247 | 5/1979 | O'Neill | 128/419 P |

Primary Examiner—Lee S. Cohen
Attorney, Agent, or Firm—Kenway & Jenney

[57] ABSTRACT

An epidural electrode lead having a resilient distal end forming a curved loop, lateral expandable loop elements, one of which is radiopaque, and an electrode contact on the lead surface opposite the loop. A withdrawable stylet maintains the distal end substantially straight during insertion of the lead into the spinal canal.

8 Claims, 5 Drawing Figures

STABILIZED DIRECTIONAL NEURAL ELECTRODE LEAD

BACKGROUND OF THE INVENTION

The present invention relates generally to neural electrodes, and in particular to a neural electrode that will remain stable in its position in the spinal canal.

Epidural electrical stimulation in the spinal cord has been shown to be effective in relieving certain types of intractable pain so that many patients can drastically reduce or even eliminate the use of pain relieving drugs when epidural stimulation is used as part of a pain treatment program. One approach to providing such electrical stimulation is to introduce an electrode into the epidural space overlying the spinal cord.

When this method is used, obtaining proper location of the electrode is usually critical. In the demyelinated, sclerosed spinal cord (as in Multiple Sclerosis), for example, there are a limited number of responsive regions along the length of the spinal cord to which the electrode should be applied. And present surgical procedures require a mid-line placement, not only to ensure that both sides of the body receive the benefits of the stimulation but also to prevent painful stimulation of the lateral margins of the spinal cord where the sensory spinal roots are found.

Generally the electrode is at the tip of a lead inserted into the spinal cord through a Touhy needle. A problem that typically occurs after placement of the lead is that of general migration. Not only does the electrode tip tend to move laterally from the ideal mid-line position (there being, in general little to prevent this) but there have been many instances of axial retraction of the tip due to tensile forces on the lead itself. This latter problem seems to accompany major activity of the back muscles, as occurs, for example, when one does push-ups.

The major contribution to the problem of electrode stability is the relatively long length of lead between the electrode tip and the site of exit from the spinal canal (some 15 to 20 cm away) where the lead is, or should be, anchored with a suture or a suturable silicone rubber clamp. The tendency of a helical lead structure, which is usually used in these procedures, is to lay straight, which is an advantageous attribute. However, this characteristic can work against the surgeon who leaves a subcutaneous loop of lead material just outside the spine such as for strain relief. The stress this creates in the loop of helical wire, which prefers a straightened configuration, places a small but constant tension upon that portion of the lead in the spinal canal, and will dislodge it unless special anchoring techniques are employed. The major problem facing any proposals for firm electrode anchoring technique relates to spinal cord sensitivity. Virtually any nontrivial forces placed upon the cord can do it permanent damage.

Accordingly it is an object of the invention to provide a neural electrode lead that will maintain its position in the spinal canal after it is inserted. It is another object to provide such a lead that will avoid injurious contact with the spinal cord. It is still another object to provide such a lead that can be used with existing tools and techniques for the insertion of leads into the spinal canal.

Further objects of the invention are to provide an effective neural electrode that is stabilized and directional in place, that is simple and economical to manufacture, and that may be easily used by medical personnel. Other objects and features of the invention will in part be apparent and in part be pointed out hereinafter.

SUMMARY OF THE INVENTION

The invention provides an epidural electrode lead having a distal end portion with a resilient portion laterally extending when a stylet is not inserted, but not extending when a stylet is inserted. The lead can be inserted into the spinal column with the stylet inserted, and the laterally extending portion can maintain the end portion in position after the stylet is withdrawn.

In the preferred form, the resilient portion is a curved loop and there are second and third loops laterally extending perpendicularly to the first loop. Also, all three loops extend from a junction with the lead to a common end point, and the electrical contact means of the lead is located adjacent the junction, opposite the first curve.

BRIEF DESCRIPTION OF THE DRAWING

For a full understanding of the nature and objects of the invention, reference should be made to the following detailed description and the accompanying drawings in which.

Corresponding reference characters indicate corresponding parts throughout the several views of the drawings.

DESCRIPTION OF A PREFERRED EMBODIMENT

Figure 1:
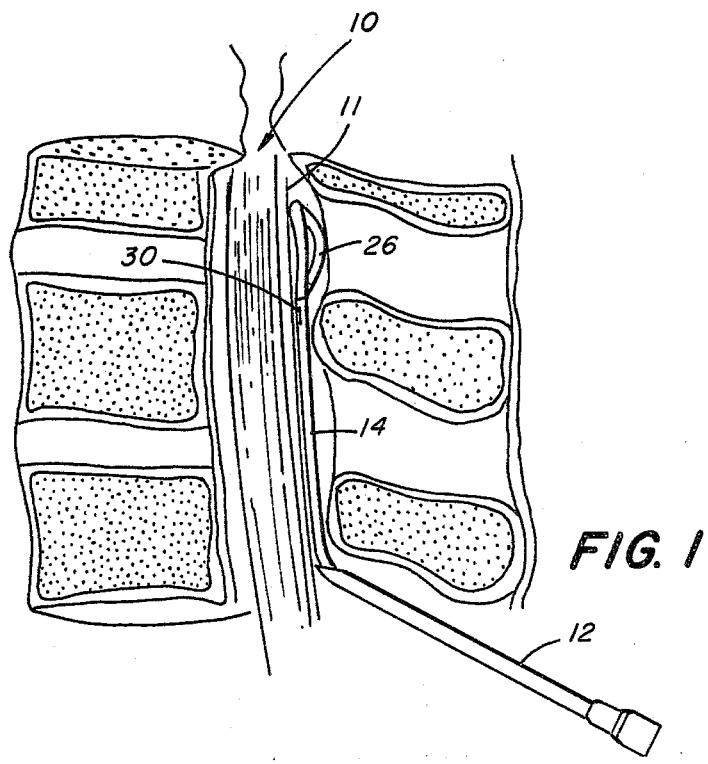
FIG. 1 is a sectional view of the spinal canal, with an epidural lead according to the invention inserted into it.

FIG. 1 shows a portion of the spinal canal 10 and illustrates the general positions of the components used in the introduction of a neural electrode to the canal for stimulation of the dura 11. The components include a Touhy needle 12 and an electrode lead 14 having a distal end 16.

Figure 2:
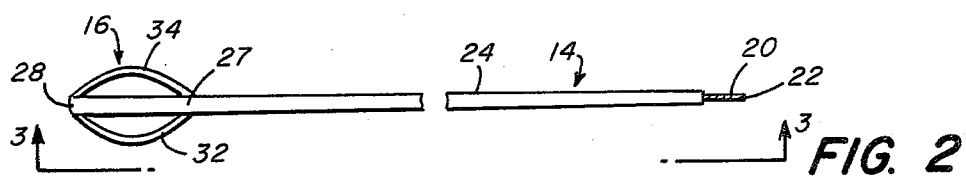
FIG. 2 is a plan view of the lead alone.
Figure 3:
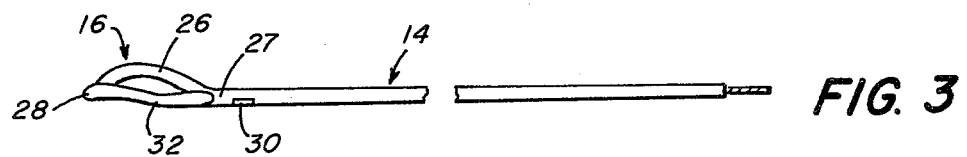
FIG. 3 is an elevation view of the lead shown in FIG. 2.

FIGS. 2 and 3 show the electrode lead 14 of the preferred embodiment. The lead 14 is an elongate member made up of a helically wound electrically conductive wire 20 defining a central tubular passage 22. An insulating sheath 24 covers the electrical conductor 20 to prevent electrical contact of the conductor 20 with any intermediate body tissue.

The distal end 16 of the lead 14 is made up of the last few centimeters of the lead. In the relaxed state shown in FIGS. 2 and 3, the lead distal end 16 forms a sinusoidal curve 26 rising from a junction 27 with the remainder of the lead 14 and terminating in an end tip 28. The distal end 16 is substantially flexible and resilient so that the preformed curve 26 may be substantially straightened by some means and still return to its curved shape when the straightening means is removed. The conductor 20 terminates in an electrical contact 30 that is located on the surface of the lead 14 opposite the curve 26 and adjacent the junction 27 of the curve with the lead. The contact 30 has a surface extending less than 180° around the lead.

Two resilient lateral stabilizers 32 and 34 extend from the sides of the distal end 16 of the lead 14. They also are generally sinusoidal in shape in the relaxed state shown in FIGS. 2 and 3, and also may be straightened and still return to the preformed curved shape. The lateral members 32 and 34 each extend in a direction perpendicular to the plane of the lead curve 26, on each side of the lead. Moreover, they each form a loop by extending from the end tip 28 of the lead to the junction 27 of the lead curve 26 with the rest of the lead 14. One of the lateral members 34, the right hand one in the embodiment, is made with a material, or is covered by one, that makes it radiopaque.

Figure 4:
FIG. 4 is a plan view of the lead with a stylet inserted.
Figure 5:
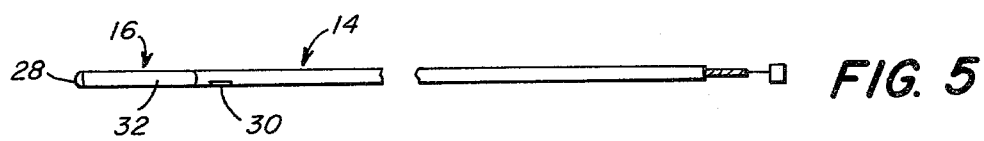
FIG. 5 is an elevation view of the lead and stylet of FIG. 4.

FIGS. 4 and 5 show the lead 14 with a stiff but slightly flexible stylet 36, with a knob 38 at the proximal end, inserted. The stylet 36 is inserted into the lead 14 via the passage 22 inside the helical conductor 20. The stylet 36 is flexible enough to bend to form the curves necessary to manipulate the lead 14 in the spinal canal 10, but stiff enough to extend the distal end 16 of the lead. As shown in FIGS. 4 and 5, holding the proximal end of the lead 14 while inserting the stylet 36 will result in extending the distal end tip 28 of the lead, straightening out the curve 26 of the lead. As curve 26 straightens, so will the curved lateral stabilizers 32 and 34, substantially straightening the distal end 16 to something not much thicker than the lead itself.

To insert the lead 14 into the spinal canal; the stylet 36 is inserted into the lead to maintain the lead curved distal end 26 and the lateral stabilizers 32 and 34 in a substantially straight configuration, allowing the lead 14 to be passed through the Touhy needle 12 into the spinal canal 10. After exiting the Touhy needle 12, the lead 14 may be moved up the spinal canal 10, assuming the Touhy needle is properly oriented. Some slight outward expansion of the lateral stabilizers 32 and 34 occurs when the lead 14 leaves the needle. The radiopaque nature of lateral stabilizer 34 allows the position and orientation of the distal end 26 of the lead to be monitored by radiographic monitors.

When the distal end 16 of the lead 14 is properly located and oriented in the spinal canal, the stylet 36 is withdrawn and the Touhy needle is also withdrawn. When the stylet 36 is withdrawn, the preformed curvature of the curve 26 of the distal end 16 reasserts itself, and the lateral members 32 and 34 extend laterally to their full lateral position as shown in FIG. 2. Since the curve 26 is beyond the junction 27 where the contact 30 is located, its reassertion into a curve from a line shape will not cause movement of the contact. The curved portion 26 extending in a plane parallel to the spine presses lightly against the wall of the spinal canal, keeping the electrical contact 30 lightly pressed forward against the dura opposite for firm electrical contact with the dura. The lateral stabilizers 32 and 34, in their expanded form, exert resistance to axial, and also lateral, movement since they too press lightly on the walls of the spinal canal.

Thus, the preformed curvature at the distal end 16 of the lead 14 forces the contact 30 gently against the dura to maintain posture independent stimulation and improve the electrode's efficiency. Some electrodes, for example, only provide effective stimulation when the patient is in the supine position while the spinal cord rests on the lead. When the patient stands or sits, the electrode is not fully contacting the dura and stimulation weakens. With the embodiment just described, the electrical contact 30 of the lead 14 will be pressed against the dura by the curved portion 26 of the lead's distal end 16, and loss of contact is less likely.

Existing leads generally end in an omni-directional cylindrical electrode tip capable of transmitting electrical current in all directions because the radial orientation of the lead may shift. The directional nature of a lead made according to the invention allows the electrical contact area to be on one side of the lead only. A directional contact will require less current to achieve the necessary current density for excitation than would an omni-directional cylindrical electrode.

Variations on the embodiment described above, in view of the purposes of the invention, may be produced by those skilled in the art. Accordingly, the invention should not be considered as confined to the embodiment shown, but should be considered to be defined by the following claims.

I claim:

1. An elongate epidural electrode lead having a distal end portion terminating in a distal end tip for insertion into the spinal canal with the aid of a stylet, comprising:
   an electrical conductor,
   an insulating sheath covering said conductor, and
   contact means located on said sheath in said distal end portion, spaced from said distal end tip, and electrically connected to said conductor for electrically contacting a portion of the spinal canal,
   said stylet being insertable in said lead for guiding said lead to its proper position in the spinal canal and removable thereafter,
   wherein the improvement comprises:
   said lead distal end portion including a resilient portion between said contact means and said distal end tip, and laterally extending when said stylet is not inserted in said lead and substantially nonextending when said stylet is inserted in said lead, whereby said lead may be inserted into the spinal canal with said stylet inserted, and said laterally extending portion may maintain said distal end portion in position after said stylet is withdrawn.

2. The epidural electrode lead of claim 1 in which said resilient portion is a curved loop.

3. The epidural electrode lead of claim 2 in which said contact means is located on said sheath opposite said resilient portion.

4. An elongate epidural electrode lead having a distal end portion for insertion into a spinal canal with the aid of a stylet comprising:
   an electrical conductor,
   an insulating sheath covering said conductor,
      said lead distal end portion having means expandable in a plane parallel to said spinal column to meet the wall of said spinal canal to hold said distal end portion in position in said canal,
   an electrode contact means connected to said conductor and located on the surface of said sheath opposite said expandable means, for contact with the dura matter of the spine, and
   laterally expandable elements located on either side of said lead distal end portion,
   whereby said stylet maintains said expandable means and expandable elements in an unexpanded mode during insertion of said lead into said spinal column.

5. An elongate epidural electrode lead having a distal end portion for insertion into the spinal canal with the aid of a stylet, comprising:
   an electrical conductor, an insulating sheath covering said conductor, and
contact means located on said distal end portion and electrically connected to said conductor for electrically contacting a portion of the spinal canal,
said stylet being insertable in said lead for guiding said lead distal end portion to its proper position in the spinal canal and removable thereafter,
wherein the improvement comprises:
said lead distal end portion including
   a first resilient curved loop portion laterally extending with respect to said sheath when said stylet is not inserted in said lead,
   second and third resilient curved loop portions laterally extending perpendicularly to said first curved loop portion when said stylet is not inserted in said lead,
   said curved loop portions substantially nonextending and aligned with said sheath when said stylet is inserted in said lead,
   whereby said lead may be inserted into the spinal canal with said stylet inserted, and said curved loop portions may maintain said distal end portion in position after said stylet is withdrawn.

6. The epidural electrode lead of claim 5 in which one of said second and third curved loop portions is radiopaque.

7. The epidural electrode lead of claim 9 in which said first curved loop portion extends from a junction with said sheath to an end point, said second and third curved loop portions extending from said junction to said end point.

8. The epidural electrode lead of claim 7 in which said contact means has a contact surface located on said sheath opposite said first curved loop portion and adjacent said junction.

* * * * *